United States Patent [19]

Fahmy

[11] 4,390,529

[45] Jun. 28, 1983

[54] S-(TERTIARY ALKYL) ALKYLPHOSPHONOAMIDODITHIOATES AND THEIR USE AS INSECTICIDES AND NEMATOCIDES

[75] Inventor: Mohamed A. Fahmy, Princeton, N.J.

[73] Assignee: Rhone-Poulenc Agrochimie, Lyons, France

[21] Appl. No.: 221,647

[22] Filed: Dec. 31, 1980

[51] Int. Cl.³ .................. A01N 57/28; C07F 9/24
[52] U.S. Cl. ..................................... 424/220; 260/959
[58] Field of Search .................. 260/959; 424/220

[56] References Cited

U.S. PATENT DOCUMENTS

| 3,010,986 | 11/1961 | Reetz | 260/959 |
| 3,018,301 | 1/1962 | Schrader | 260/959 |
| 3,185,721 | 5/1965 | Schrader | 260/959 |

Primary Examiner—Anton H. Sutto
Attorney, Agent, or Firm—Burns, Doane, Swecker & Mathis

[57] ABSTRACT

Compounds having the formula

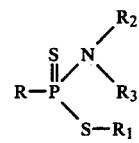

in which

R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;

$R_1$ is tertiary alkyl of 4 to 8 carbon atoms; and $R_2$ and $R_3$, independently are hydrogen, alkyl of 1 to 8 carbon atoms or cycloalkyl are disclosed as well as their use as insecticides and nematocides, e.g., in controlling Corn rootworm and Southern Armyworm.

26 Claims, No Drawings

S-(TERTIARY ALKYL) ALKYLPHOSPHONOAMIDODITHIOATES AND THEIR USE AS INSECTICIDES AND NEMATOCIDES

CROSS-REFERENCE TO RELATED APPLICATIONS

An application entitled "BRANCHED-S-ALKYL PHOSPHONODITHIOIC HALIDE INTERMEDIATES AND PROCESS FOR THEIR PRODUCTION", Ser. No. 071,465, filed on Aug. 31, 1979 in the name of Mohamed A. Fahmy, abandoned in favor of continuation application Ser. No. 201,937, filed on Oct. 29, 1980, now pending, discloses certain intermediates useful for the production of insecticides and nematocides of this invention and the process for their preparation.

SUMMARY OF THE INVENTION

This invention relates to S-(tertiary alkyl)alkylphosphonoamidodithioate compounds and their use as insecticides and nematocides.

More particularly, the compounds of the invention have the formula $$R-\underset{SR_1}{\overset{S}{\underset{\|}{P}}}-N\overset{R_2}{\underset{R_3}{\diagdown}}$$

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is tertiary alkyl of 4 to 8 carbon atoms; and
$R_2$ and $R_3$, independently, are hydrogen, alkyl of 1 to 8 carbon atoms or cycloalkyl.

These compounds exhibit a wide range of insecticidal activity and are of particular interest in controlling Corn rootworm and Southern Armyworm because of their stability and long residual activity.

DETAILED DESCRIPTION OF THE INVENTION

An important structural feature of the compounds of this invention is that $R_1$ in the above formula is tertiary alkyl. Certain S-alkyl alkylphosphonoamidodithioate compounds are described in U.S. Pat. No. 3,636,206 and in Akamsin V. D. et al., Izvestiya Akodemi Nauk SSSR, Seriya Khimicheskaya, No. 9, pp. 1983–1986, Sept. 1967. However, none of the species described in the foregoing prior art correspond to the above formula where $R_1$ is tertiary alkyl. It has been found that the tertiary alkyl compounds of this invention possess high toxicity to Southern Armyworm and Corn rootworm, for example.

The compounds disclosed herein can be prepared by using a starting material which is a S-(tertiary alkyl)alkylphosphonodithioic halide, the preparation of which is illustrated in Example 1. A more detailed description of the preparation of these starting materials is contained in an application by M. Fahmy, Ser. No. 071,465, filed on Aug. 31, 1979, abandoned in favor of continuation application Ser. No. 201,937, filed on Oct. 29, 1980, now pending, which application is incorporated herein by reference. The S-(tertiary alkyl)alkylphosphonodithioic halide is reacted with ammonia, or an amine in the presence of a solvent to arrive at the compounds of this invention.

The preferred reaction scheme is as follows:

$$R-\underset{SR_1}{\overset{S}{\underset{\|}{P}}}-X + 2HN\overset{R_2}{\underset{R_3}{\diagdown}} \longrightarrow R-\underset{SR_1}{\overset{S}{\underset{\|}{P}}}-N\overset{R_2}{\underset{R_3}{\diagdown}} + \overset{R_2}{\underset{R_3}{\diagdown}}NH\cdot HX$$

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is tertiary alkyl of 4 to 8 carbon atoms; $R_2$ and $R_3$, independently, are hydrogen, alkyl of 1 to 8 carbon atoms or cycloalkyl; and
X is halogen.

$R_1$ is preferably tertiary-butyl or tertiary amyl.

The cycloalkyl group is preferably cyclopentyl or cyclohexyl.

The halogen X is preferably chloro.

The reaction is advantageously carried out at a temperature of about 0° C. to 100° C. in an organic solvent, water or aqueous organic solvent.

Suitable organic solvents are water miscible solvents, such as acetone, which do not participate in the reaction themselves.

The compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, non-phytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well-known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 kg/hectare. Under ideal conditions, depending on the pest to be controlled, the lower rate may offer adequate protection. On the other hand, adverse weather conditions, resistance of the pest and other factors may require that the active ingredient be used in higher proportions.

When the pest is soil-borne, the formulation containing the active ingredient is distributed evenly over the area to be treated in any convenient manner. The active component can be washed into the soil by spraying with water over the area or can be left to the natural action of rain-fall. After application, the formulation can be distributed in the soil by plowing or disking. Application can be prior to planting, after planting but before sprouting has taken place or after sprouting.

The following examples illustrate the preparation of the compounds of this invention and their pesticidal properties. It will be understood that all of the compounds disclosed herein can be prepared by methods analogous to those described below.

EXAMPLE 1

Preparation of S-tert-butyl ethylphosphonodithioic chloride (Intermediate)

To a solution of ethylphosphonothioic dichloride (80 g, 0.5 mol) in 500 ml dry toluene, was added 2-methyl-2-propanethiol (50 g, 0.55 mol). The solution was stirred while triethylamine (60 g, 0.6 mol) was added dropwise. After the complete addition of the amine, the mixture was stirred and heated up to 80° C. for three hours and allowed to stand overnight. The reaction mixture was washed with 5% cold HCl solution (100 ml), followed by another wash with 5% cold NaOH solution (100 ml), finally washed twice with water (100 ml each), and dried over magnesium sulfate. Toluene was evaporated under a water aspirator vacuum, and the oil residue was distilled. The product distilled at 78°–80° C./0.2 mm. The yield was 60 g (55.4% of theoretical yield). The structure was confirmed by NMR.

EXAMPLE 2

Preparation of S-(tertiary butyl) ethylphosphonoamidodithioate.

To solution of 10 g of S-tert-butyl ethylphosphonodithioc chloride (0.046 mol) in 30 ml acetone (cooled to about 2° C.) was added 10 ml of concentrated ammonium hydroxide (0.015 mol) dropwise while maintaning the temperature around 5°–10° C. The reaction mixture was stirred at room temperature for 1 hour. The solvents were stripped off by a flash evaporator, and the residue was extracted with methylene chloride. The methylene chloride extract was filtered and the solvent was removed under vacuum. The residual oil was subjected to high vacuum (0.1 mm). After about 1 hour under vacuum, the liquid transformed into solid wax. Yield about 6.5 g (75% yield).

H-NMR of the product confirmed the structure.

EXAMPLES 3–6

In a manner similar to that illustrated in Example 2 and by substituting the appropriate amine for ammonia in Examples 4–6 compounds with the following structure were prepared.

| EXAMPLE | R | $R_1$ | $R_2$ | $R_3$ |
|---|---|---|---|---|
| 3 | $CH_3$ | $C(CH_3)_3$ | H | H |
| 4 | $C_2H_5$ | $C(CH_3)_3$ | H | $CH_3$ |
| 5 | $CH_3$ | $C(CH_3)_3$ | H | $CH(CH_3)_2$ |
| 6 | $C_2H_5$ | $C(CH_3)_3$ | H | $CH(CH_3)_2$ |

EXAMPLE 7

Testing for Corn rootworm intrinsic activity, and activity against Southern Armyworm.

A. Corn Rootworm Intrinsic Activity (CRW)

The test compound is prepared in a one percent solution with acetone or ethanol. The stock solution is then diluted with an aqueous solution of Tween-20 and water to the appropriate concentration (i.e., 100, 10, 1, 0.1, 0.005 ppm). Two ml of this solution is pipetted into a 9 cm petri dish containing two layers of filter paper. Second instar larvae are introduced and the dish closed. Observations for mortality and moribund larvae are made after two days (48 hours) exposure. Insecticidal activity is primarily contact and vapor action with minimum ingestion. The results are tabulated in Table 1.

B. Southern Armyworm Intrinsic Activity (SAW)

Stock solution (1%) of test material was made in acetone and diluted to the desired concentration by a 500 ppm Tween-20 aqueous solution. Lima bean leaves are dipped into the solution and transferred to petri dishes (100×15 mm) containing two filter papers moistened with 2 ml water. Each petri dish contained one leaf and was kept open to dry out the solution on the leaf. Five third instar larvae of Southern Armyworm (*Spodoptera eridania*) were added to the leaf and the dish was finally covered.

The insects were held at 78° F. for 72 hours and percent kill was recorded. The results are tabulated in Table 1.

TABLE 1

| | % Kill | | | |
|---|---|---|---|---|
| | SAW | | CRW Rate (ppm) | |
| EXAMPLE | 500 | 100 | 1 | 0.1 |
| 2 | 100 | 85 | 85 | 25 |
| 3 | 100 | 75 | 40 | 0 |
| 4 | 80 | — | 100 | 35 |
| 5 | 100 | 80 | 95 | 10 |
| 6 | 100 | 55 | 95 | 10 |

I claim:

1. A method for controlling insects or nematodes which comprises applying thereto or to their habitat, in an amount pesticidal to said insects or nematodes, a compound of the formula

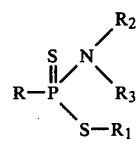

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;

$R_1$ is tertiary alkyl of 4 to 8 carbon atoms; and
$R_2$ and $R_3$, independently, are hydrogen, alkyl of 1 to 8 carbon atoms, cyclopentyl or cyclohexyl.

2. A method for controlling Corn rootworm which comprises providing in the soil, in an amount pesticidal to Corn rootworm, a compound of the formula

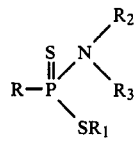

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is tertiary alkyl of 4 to 8 carbon atoms; and
$R_2$ and $R_3$, independently, are hydrogen, alkyl of 1 to 8 carbon atoms, cyclopentyl or cyclohexyl.

3. The method of claim 2 in which R is alkyl of 1 to 8 carbon atoms.

4. The method of claim 2 in which R is methyl or ethyl.

5. The method of claim 2 in which $R_1$ is tert-butyl or tert-amyl.

6. The method of claim 2 in which R is methyl or ethyl;
$R_1$ is tert-butyl;
$R_2$ is hydrogen; and
$R_3$ is isopropyl.

7. A compound of the formula

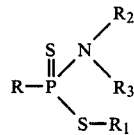

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is tertiary alkyl of 4 to 8 carbon atoms; and
$R_2$ and $R_3$, independently are hydrogen, alkyl of 1 to 8 carbon atoms, cyclopentyl or cyclohexyl.

8. A compound of claim 7 in which R is alkyl of 1 to 8 carbon atoms.

9. A compound of claim 7 in which $R_1$ is tert-butyl or tert-amyl.

10. A compound of claim 7 in which R is methyl or ethyl.

11. A compound of claim 7 in which $R_2$ and $R_3$ are hydrogen.

12. A compound of claim 7 in which
R is methyl or ethyl;
$R_1$ is tert-butyl or tert-amyl; and
$R_2$ and $R_3$ are hydrogen.

13. A compound of claim 7 in which
R is ethyl;
$R_1$ is tert-butyl;
$R_2$ is hydrogen; and
$R_3$ is isopropyl.

14. A compound of claim 7 in which
R is methyl;
$R_1$ is tert-butyl;
$R_2$ is hydrogen; and
$R_3$ is isopropyl.

15. A compound of claim 7 in which $R_1$ is tert-butyl.

16. A compound of claim 7 in which R is methyl.

17. A compound of claim 7 in which R is ethyl.

18. A compound of claim 7 in which $R_2$ is hydrogen and $R_3$ is alkyl of 1 to 8 carbon atoms.

19. A compound of claim 7 in which $R_2$ is hydrogen and $R_3$ is methyl.

20. A compound of claim 7 in which $R_2$ is hydrogen and $R_3$ is isopropyl.

21. A compound of claim 7 in which
R is ethyl;
$R_1$ is tert-butyl; and
$R_2$ and $R_3$ are hydrogen.

22. A compound of claim 7 in which
R is methyl;
$R_1$ is tert-butyl; and
$R_2$ and $R_3$ are hydrogen.

23. A compound of claim 7 in which:
R is ethyl;
$R_1$ is tert-butyl;
$R_2$ is hydrogen; and
$R_3$ is methyl.

24. A composition for use in controlling insects or nematodes comprising, as the active ingredient, a compound of the formula:

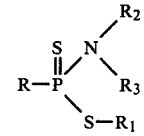

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is tertiary alkyl of 4 to 8 carbon atoms; and
$R_2$ and $R_3$, independently, are hydrogen, alkyl of 1 to 8 carbon atoms, cyclopentyl or cyclohexyl, in an amount effective as an insecticide or nematocide, and an inert, non-phytotoxic organic solvent or solid carrier.

25. The composition of claim 24 in which R is alkyl.

26. The composition of claim 24 in which $R_1$ is tert-butyl or tert-amyl.

* * * * *